US00PP24169P2

(12) United States Plant Patent
Hull

(10) Patent No.: US PP24,169 P2
(45) Date of Patent: Jan. 21, 2014

(54) ***TECOMA* PLANT NAMED 'TEC60109105'**

(50) Latin Name: *Tecoma stans*
Varietal Denomination: TEC60109105

(76) Inventor: George Edward Hull, Phoenix, AZ (US)

( * ) Notice: Subject to any disclaimer, the term of this patent is extended or adjusted under 35 U.S.C. 154(b) by 150 days.

(21) Appl. No.: 13/317,869

(22) Filed: Oct. 31, 2011

(51) Int. Cl.
*A01H 5/00* (2006.01)

(52) U.S. Cl.
USPC ..... Plt./226

(58) Field of Classification Search
USPC ..... Plt./226, 263.1
See application file for complete search history.

*Primary Examiner* — Howard Locker

(57) ABSTRACT

A new cultivar of *Tecoma* plant named 'TEC60109105' that is characterized by yellow flowers, early spring flowering, short internodes, light green leaves and very few seed pods.

1 Drawing Sheet

Botanical classification: *Tecoma stans*.
Variety denomination: 'TEC60109105'.

BACKGROUND OF THE INVENTION

The present invention relates to a new and distinct cultivar of *Tecoma* plant botanically known as *Tecoma stans* and hereinafter referred to by the cultivar name 'TEC60109105'.

The new *Tecoma* cultivar is the product of a breeding program conducted by the inventor in Gilbert, Ariz. The objective of the breeding program is to create new *Tecoma* cultivars with interesting flower colors and a compact habit.

'TEC60109105' originated from a crossing in 2008 of the female or seed parent an unnamed *Tecoma* plant (not patented) and the male or pollen parent an unnamed *Tecoma* plant (not patented). The resulting seeds were subsequently planted and grown. The cultivar 'TEC60109105' was selected by the inventor in 2009 as a single plant within the progeny of the stated cross in Gilbert, Ariz.

Asexual reproduction of the new cultivar 'TEC60109105' first occurred by terminal cuttings of young herbaceous shoots in 2009 in Gilbert, Ariz. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Tecoma* cultivar 'TEC60109105'. These traits in combination distinguish 'TEC60109105' as a new and distinct cultivar apart from other existing known varieties of *Tecoma*.

1. *Tecoma* 'TEC60109105' exhibits yellow flowers.
2. *Tecoma* 'TEC60109105' exhibits year round flowering.
3. *Tecoma* 'TEC60109105' exhibits short internodes.
4. *Tecoma* 'TEC60109105' exhibits light green leaves.
5. *Tecoma* 'TEC60109105' exhibits very few seed pods.

The closest comparison cultivar is *Tecoma* 'Gold Star' (not patented).

'TEC60109105' is distinguishable from 'Gold Star' by the following characteristics:

1. 'TEC60109105' has shorter internodes than 'Gold Star'.
2. 'TEC60109105' has flowers that bloom earlier in Spring than the flowers of 'Gold Star'.
3. 'TEC60109105' has very few seed pods. 'Gold Star' produces a large number of seed pods.

BRIEF DESCRIPTION OF THE DRAWING

The accompanying photograph illustrates the distinguishing traits of *Tecoma* 'TEC60109105'. The plant in the photograph shows an overall view of a 12 month old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Tecoma* cultivar named 'TEC60109105'. Data was collected in Gilbert, Ariz. from 12 month old outdoor grown plants in 3 gallon containers. The time of year was Summer and the temperature range was 26-37 degrees Centigrade during the day and 15-21 degrees Centigrade at night. Color determinations are in accordance with The Royal Horticultural Society Colour Chart 2007 edition, except where general color terms of ordinary dictionary significance are used. The growing requirements are similar to the species. 'TEC60109105' has not been tested under all possible conditions and phenotypic differences may be observed with variations in environmental, climatic, and cultural conditions, however, without any variance in genotype.

Botanical classification: *Tecoma stans* 'TEC60109105'.
Parentage: 'TEC60109105' is the product of an unnamed *Tecoma* female or seed parent *Tecoma* and an unnamed *Tecoma* male or pollen parent.
Vigor: Moderate.
Plant type: Perennial Shrub.
Growth habit: Upright.
Plant shape: Slight inverted triangle.
Suitable container size: 2 to 5 gallon containers.
Height: 48 cm.
Width: 40 cm.

Low temperature tolerance: 0° Centigrade.
High temperature tolerance: 50° Centigrade.
Propagation: Softwood cuttings.
Time to initiate roots in summer: 10 days to initiate roots at 32° Centigrade.
Time to initiate roots in winter: 25 days to initiate roots at 15° Centigrade.
Time to produce a rooted cutting or liner in summer: 21 days at 32° Centigrade.
Time to produce a rooted cutting or liner in winter: 45 days at 15° Centigrade.
Crop time: Approximately 12 weeks.
Root system: Fine and fibrous.
Stem:
*Pinching.*—Removal of young shoot tips is required to produce a dense bushy plant.
*Lateral branch diameter.*—5 mm. in diameter.
*Lateral branch length.*—20 cm. in length.
*Internode length.*—5 cm.
*Stem shape.*—Round.
*Stem strength.*—Strong.
*Stem color.*—144A.
*Pubescence.*—Absent.
Foliage:
*Leaf arrangement.*—Opposite.
*Compound or single.*—Odd pinnate compound.
*Number of leaves per lateral branch.*—15 to 20.
*Quantity of leaflets per leaf.*—7 to 11.
*Leaf shape.*—Lanceolate.
*Leaf apex.*—Acuminate.
*Leaf base.*—Unequal obtuse.
*Terminal leaf dimensions.*—17 cm. in length and 11 cm. in width.
*Leaflet dimensions.*—5.5 cm. in length and 2.5 cm. in width.
*Texture.*—Glaucous both sides.
*Pubescence.*—Absent.
*Leaf margin.*—Serrate.
*Venation pattern.*—Pinnate.
*Young leaf color* (*upper surface*).—137B.
*Young leaf color* (*lower surface*).—137C.
*Mature leaf color* (*upper surface*).—137A.
*Mature leaf color* (*lower surface*).—137C.
*Vein color* (*under surface*).—151A.
*Leaf attachment.*—Petiolate.
*Petiole dimensions.*—3.7 cm. in length and 2 mm. in diameter.
*Petiole color.*—151 A.
*Durability of foliage to stress.*—Strong.
Flower:
*Inflorescence arrangement.*—Raceme.
*Inflorescence dimensions.*—14 cm. in height and 14 cm. in width.
*Quantity of flowers per inflorescence.*—6.
*Quantity of flowers per lateral stem.*—6.
*Quantity of flowers and buds per plant.*—Average 72.
*Natural flowering season.*—All year in Central and Southern Arizona.
*Fragrance.*—None.
*Flower bud length.*—5 cm.
*Flower bud diameter.*—1 cm.
*Flower bud shape.*—Ovate.
*Bud color.*—7A.
*Flower aspect.*—Outward.
*Flower shape.*—Salverform.
*Flower dimensions.*—3.5 cm. in diameter and 5 cm. in height.
*Flower longevity.*—7 days.
*Number of petals.*—5.
*Fused or unfused.*—Fused.
*Petal shape.*—Spatulate.
*Petal margin.*—Entire.
*Petal texture.*—Smooth.
*Petal apex.*—Rounded.
*Petal base.*—Fused.
*Petal length.*—1.5 cm above fuse.
*Petal width.*—1.5 cm.
*Petal color when opening* (*upper side*).—12A.
*Petal color when opening* (*under side*).—12A.
*Petal color fully opened* (*upper side*).—12A.
*Petal color fully opened* (*under side*).—12A.
*Petal color fading to.*—10C.
*Self-cleaning or persistent.*—Self-cleaning.
Calyx:
*Calyx dimensions.*—9 mm. in length and 4 mm. in diameter.
Peduncle:
*Peduncle dimensions.*—1 cm. in length and 2 mm. in diameter.
*Peduncle angle.*—90 degrees from vertical.
*Peduncle strength.*—Strong.
*Peduncle color.*—151 C.
Reproduction organs:
*Stamen number.*—5.
*Anther length.*—7 mm.
*Anther color.*—2D.
*Amount of pollen.*—Medium.
*Pistil number.*—1.
*Stigma shape.*—Bifurcated.
*Stigma color.*—2D.
*Style length.*—3.5 cm.
*Style color.*—2D.
*Ovary color.*—147C.
Fruit:
*Quantity of fruit per lateral branch.*—One.
*Fruit dimensions.*—8 cm. in length and 1.3 cm. in width.
*Fruit color.*—Young fruit 144A, mature fruit 199A.
*Quantity of seeds per pod.*—40 to 60.
*Seed dimensions.*—7 mm. in length and 3 mm. in width.
Disease and pest resistance: Disease and pest resistance has not been observed.

The invention claimed is:

1. A new and distinct variety of *Tecoma* plant named 'TEC60109105' as described and illustrated.

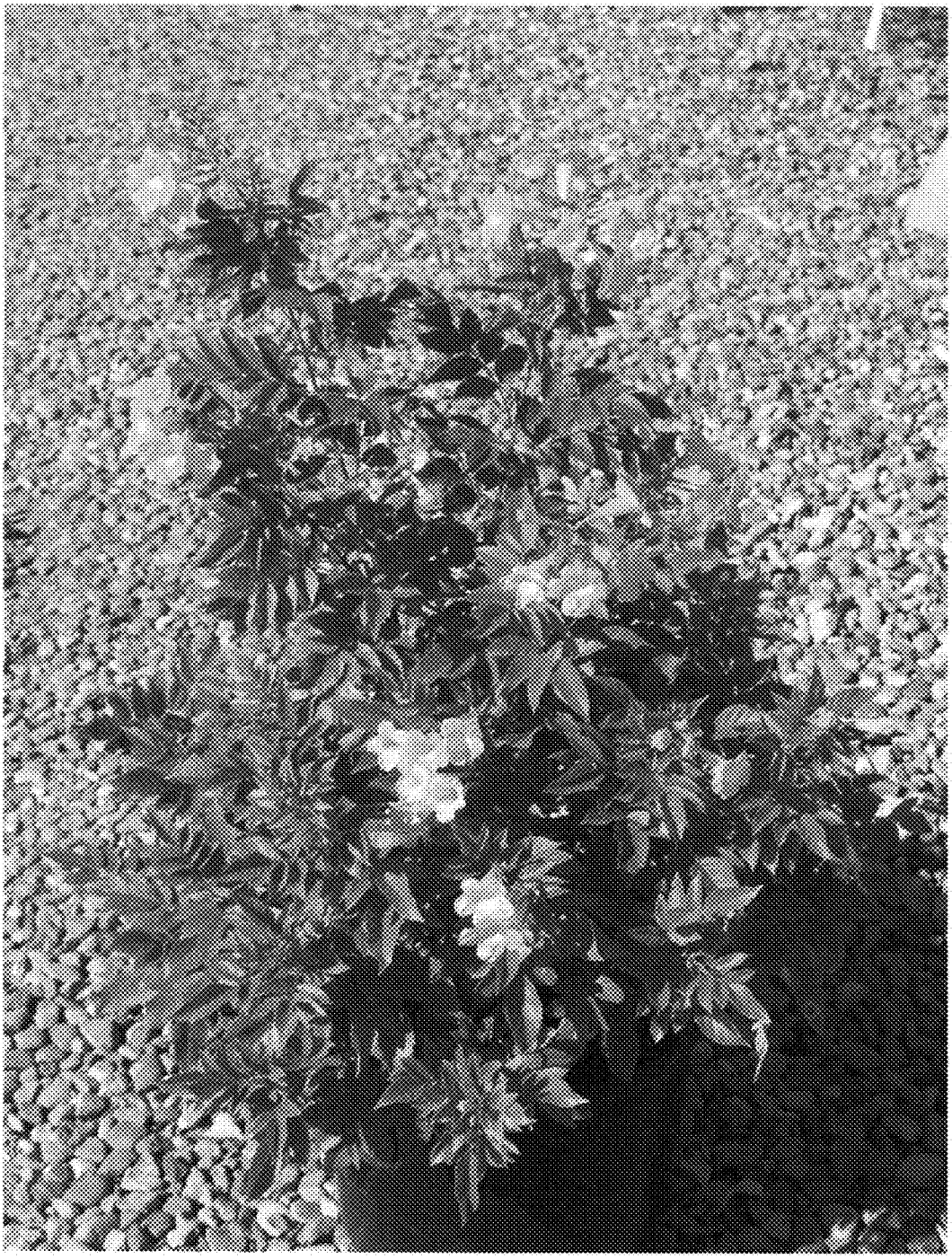

* * * * *